United States Patent
Lin et al.

(10) Patent No.: US 6,657,545 B1
(45) Date of Patent: Dec. 2, 2003

(54) AUTOMATIC DETECTING AND PREWARNING SYSTEM FOR MEDICINE INSTILLER

(76) Inventors: Yu-Yueh Lin, 3F, No. 17, Jiang S. St., Neihu Chiu, Taipei (TW); Kan-Jung Yang, No. 40, Lane 113, Hangjou Rd., Jungli City, Taoyuan (TW)

( * ) Notice: Subject to any disclaimer, the term of this patent is extended or adjusted under 35 U.S.C. 154(b) by 0 days.

(21) Appl. No.: 10/188,759

(22) Filed: Jul. 5, 2002

(51) Int. Cl.[7] .......................... G08B 21/00; A61M 5/14
(52) U.S. Cl. ...................... 340/606; 340/624; 340/623; 340/618; 128/214
(58) Field of Search ............................. 340/624, 618, 340/623; 604/254; 128/214

(56) References Cited

U.S. PATENT DOCUMENTS

| 3,871,229 A | * | 3/1975 | Fletcher ................... 73/861.41 |
| 4,038,982 A | * | 8/1977 | Burke et al. ................. 604/65 |
| 6,337,631 B1 | * | 1/2002 | Pai et al. .................... 340/618 |

FOREIGN PATENT DOCUMENTS

GB    2199405 A    *    7/1988    ........... A61M/5/14

* cited by examiner

Primary Examiner—Benjamin C. Lee
Assistant Examiner—Lam Pham
(74) Attorney, Agent, or Firm—Troxell Law Office PLLC

(57) ABSTRACT

An automatic detecting and prewarning system for medicine instiller mainly includes a clamp for easily clamping on a flow-indicating cylinder of the medicine instiller, detecting means of an electronic sensor type mounted on the clamp, alarm means connected to the detecting means via a conductor, and a drop carrier pivotally connected to a lever to locate in the flow-indicating cylinder below a medicine dropper. After a fixed number of drops or flow per minute is set for the medicine instiller and input to the alarm means, medicine drops fallen from the medicine dropper one by one impact on and reciprocatingly sway the drop carrier to intermittently cut off the detecting means as a control signal to the alarm means. When an abnormal number of drops or flow per minute continues for a preset time, the alarm means is automatically enabled to emit warnings.

4 Claims, 4 Drawing Sheets

AUTOMATIC DETECTING AND PREWARNING SYSTEM FOR MEDICINE INSTILLER

FIELD OF THE INVENTION

The present invention relates to an automatic detecting and prewarning system for medicine instiller, in which a drop carrier is pivotally connected to a lever to locate in a flow-indicating cylinder below a medicine dropper of the medicine instiller. Medicine drops fall from the medicine dropper at a preset speed or flow to impact on and reciprocatingly sway the drop carrier and thereby intermittently cut off detecting means of the system as a control signal to alarm means thereof. When an abnormal instilling speed or flow continues for a preset time, the alarm means is automatically enabled to emit warnings.

BACKGROUND OF THE INVENTION

Medicine instillation is frequently used in medical treatments. Conventionally, a medicine liquid being instilled is visually examined by nursing personnel for normal instillation speed and remained volume thereof. Currently, there are also electronic instruments developed for controlling dosage, time, and flow of instilled medicine liquid. However, these electronic instruments usually have a large volume and are expensive in price, and are therefore normally employed by medical organizations only in special medicine liquids that require particularly attention to the instilling time and flow thereof.

There is also developed a sensing needle connected to a sensing circuit and alarm means for directly piercing into a medicine bag or bottle containing a medicine liquid to be instilled. Since the sensing needle must be in contact with the medicine liquid to work, it is not disposable to meet sanitary requirements.

An invention entitled "Method and Apparatus for Monitoring the Level of the Contents in a Container" was laid open by European Patent Office under Publication No. EP370604A1 on May 30, 1990. However, the disclosed monitor and method for monitoring the level of the contents in a container is not highly convenient for use.

U.S. Pat. No. 6,337,631 B1 granted to the same applicant of the present invention discloses an alarm system that is automatically enabled to produce warnings when an instilled medicine liquid is about used up. However, further improvements could still be made to this patented invention.

SUMMARY OF THE INVENTION

A primary object of the present invention is to provide an automatic detecting and prewarning system for medicine instiller. The system includes a clamp for easily clamping on a flow-indicating cylinder of the medicine instiller, detecting means of an electronic sensor type mounted on the clamp, alarm means connected to the detecting means via a conductor, and a drop carrier pivotally connected to a lever to locate in the flow-indicating cylinder below a medicine dropper. After a fixed number of drops or flow per minute is set for the medicine instiller and input to the alarm means, medicine drops fallen from the medicine dropper one by one impact on and reciprocatingly sway the drop carrier to intermittently cut off the detecting means as a control signal to the alarm means. When an abnormal number of drops or flow per minute continues for a preset time, which might be caused by a compressed and bent tube of the medicine instiller, an empty medicine container, etc., the alarm means is automatically enabled to emit warnings.

Another object of the present invention is to provide an automatic detecting and prewarning system for medicine instiller, with which a fixed number of drops or flow per minute of the medicine instiller can be detected and calculated for inputting to alarm means of the system, so that a time point at which the instilled medicine liquid is about used up may be determined in advance with the help of currently available electronic controlling technologies. This function enables nursing personnel to watch several medicine instillers at the same time to achieve effective control and management of patient wards and high efficient nursing.

BRIEF DESCRIPTION OF THE DRAWINGS

The structure and the technical means adopted by the present invention to achieve the above and other objects can be best understood by referring to the following detailed description of the preferred embodiments and the accompanying drawings, wherein.

DETAILED DESCRIPTION OF THE PREFERRED EMBODIMENTS

Figure 1:
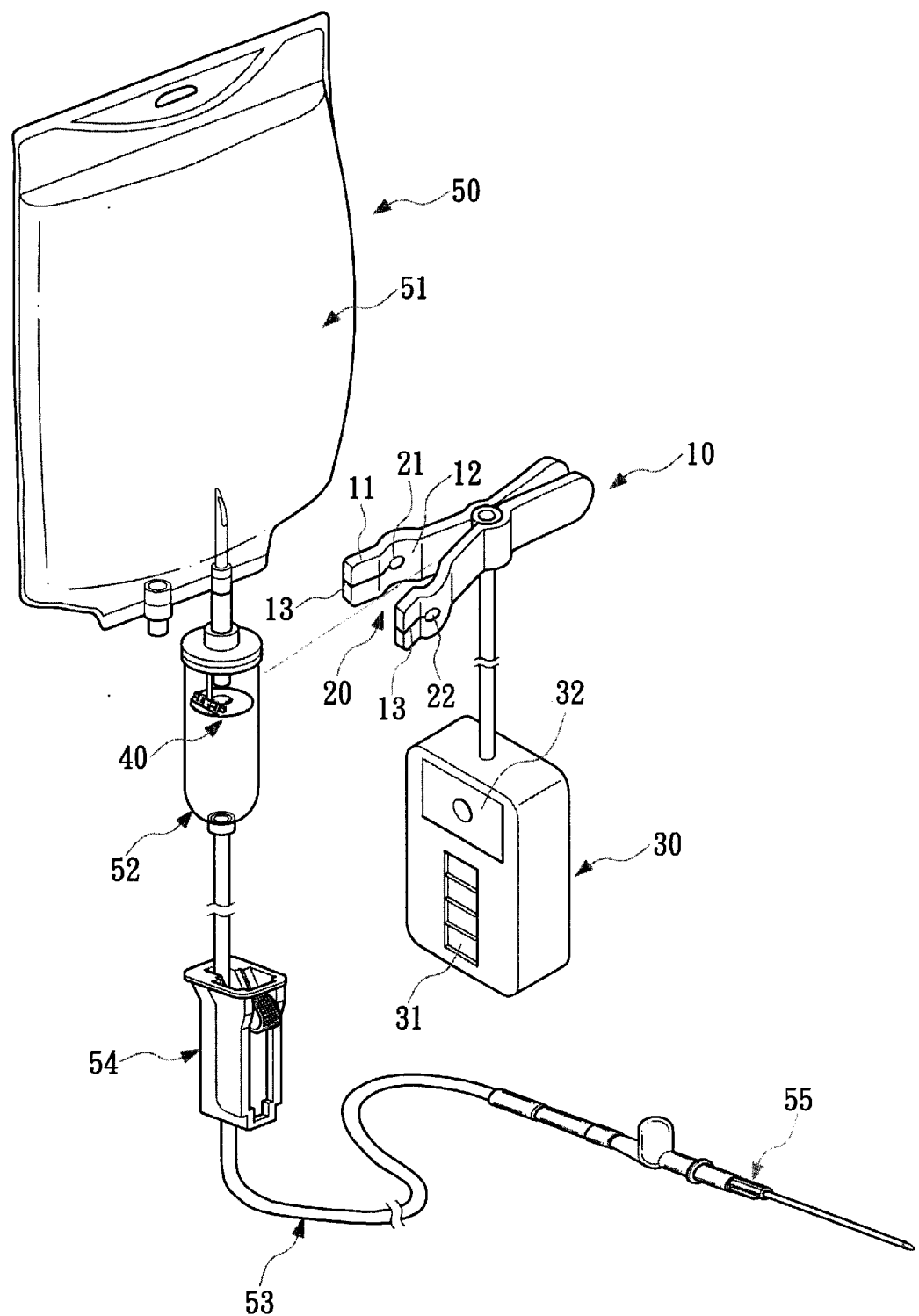
FIG. 1 is a perspective view showing an embodiment of the automatic detecting and prewarning system of the present invention and a medicine instiller to which the system of the present invention is connected.
Figures 2, 3:
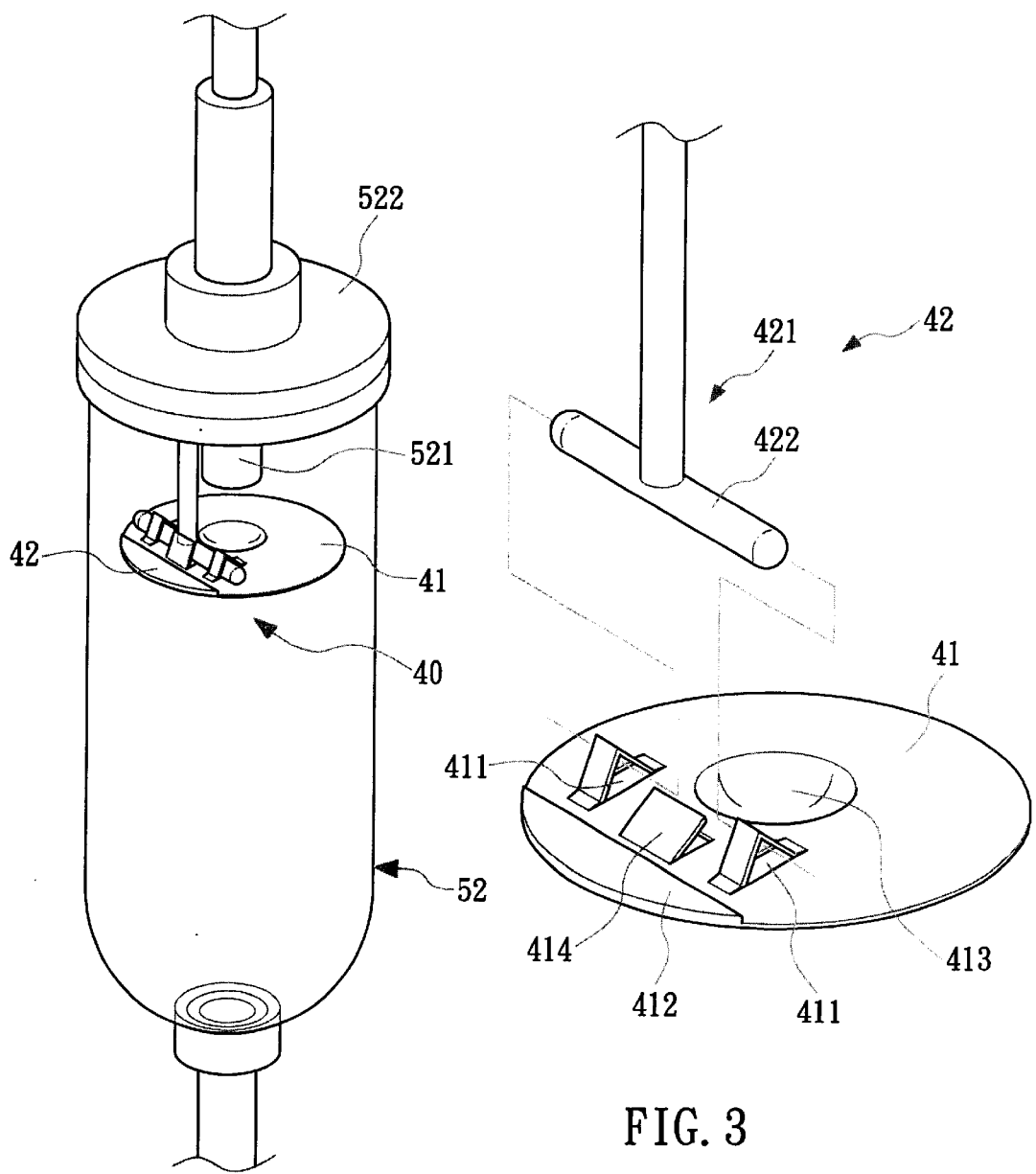
FIG. 2 is a fragmentary and enlarged view of FIG. 1 showing a flow-indicating cylinder included in the medicine instiller.
FIG. 3 is an exploded and enlarged perspective view of a drop carrier included in the system of the present invention.

Please refer to FIGS. 1, 2, and 3 in which an automatic detecting and prewarning system for medicine instiller according to an embodiment of the present invention is shown. A medicine instiller 50 normally includes a medicine container 51 containing an amount of medicine liquid, a transparent flow-indicating cylinder 52, a tube 53, a flow controller 54, and a syringe 55. The system of the present invention mainly includes a clamp 10, detecting means 20 provided on the clamp 10, alarm means 30 connected to the detecting means 20, and drop-carrier swaying means 40. The clamp 10 is adapted to clamp on the flow-indicating cylinder 52 at a predetermined position without compressing or deforming the latter.

The clamp 10 may be differently designed so long as it could be easily clamped onto and removed from the flow-indicating cylinder 52 for repeated use. In the illustrated embodiment of the present invention of FIG. 1, the clamp 10 is a properly sized elastic clamp having two jaws 11. The two jaws 11 are provided with an outward curved portion 12 each, so that they could be opened apart to fitly enclose an outer surface of the flow-indicating cylinder 52 with the curved portions 12. Two horizontal markers 13 may be correspondingly provided at free ends of the two jaws 11 to facilitate easy locating of the clamp 10 on the flow-indicating cylinder 52 without hindering nursing personnel from visually inspecting an internal condition of the flow-indicating cylinder 52.

Figure 4:
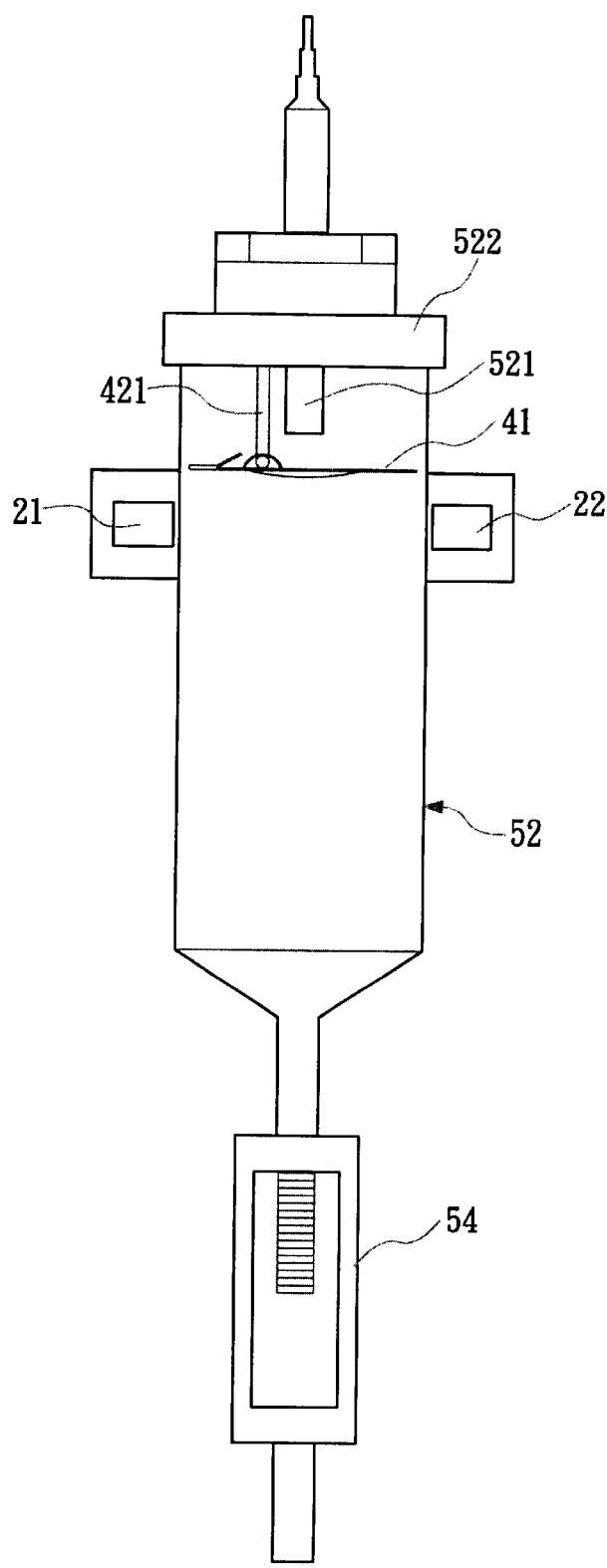
FIG. 4 is a fragmentary side view of the system of the present invention showing the drop carrier in an empty and horizontal state.

The detecting means 20 is mounted on the two jaws 11 of the clamp 10, and is designed according to general infrared emission and reception principle. In addition to infrared, magnetic waves, laser, etc., may also be used for the detecting means 20. The detecting means 20 includes an emitter 21 and a receiver 22, which are separately but correspondingly located at inner sides of the curved portions 12 of the two jaws 11 of the clamp 10. When the clamp 10 is clamped on the transparent flow-indicating cylinder 52, the emitter 21 and the receiver 22 are spaced by the transparent cylinder 52 to face-each other, as shown in FIG. 4. With the emitter 21 and the receiver 22 at the above-described positions, the detecting means 20 provides its detecting function using a direct light or wave transmitted from the emitter 21 to the receiver 22. The above-mentioned markers 13 are provided on the free ends of the two jaws 11 of the clamp 10 corresponding to the emitter 21 and the receiver 22.

The alarm means 30 is internally provided with related electronic control circuits, which could be controlled via switches 31 provided at an outer side of the alarm means 30. An external display 32 is provided to show related data for nursing personnel's reference in operating or monitoring the automatic detecting and prewarning system of the present invention.

Please refer to FIG. 2 that is a fragmentary and enlarged perspective view showing an internal structure of the flow-indicating cylinder 52. The flow-indicating cylinder 52 includes a medicine dropper 521 and an upper cap 522, through a center of which the medicine dropper 521 is downward extended into the cylinder 52. The drop-carrier swaying means 40 is disposed in the flow-indicating cylinder 52 below the medicine dropper 521 in any acceptable manner, so as to locate at a fixed height in the cylinder 52.

Please refer to FIG. 3 that is an exploded perspective view of the drop-carrier swaying means 40. As shown, the drop-carrier swaying means 40 mainly includes a drop carrier 41, and a lever structure 42 enabling the drop carrier 41 to sway. Both the drop carrier 41 and the lever structure 42 may be differently designed to provide equivalent function. According to the drop-carrier swaying means 40 illustrated in FIG. 3, the lever structure 42 includes an inverted T-shaped holder 421 having a vertical support downward extended from a bottom of the upper cap 522 of the flow-indicating cylinder 52, and a horizontal shaft 422 connected to a lower end of the vertical support; and the drop carrier 41 is a disc member having predetermined dimensions suitable for positioning in the cylinder 52. The drop carrier 41 is provided on a top near one side with two laterally symmetrical shaft holes 411, into which the horizontal shaft 422 may be easily extended to serve as a lever shaft for the drop carrier 41 to sway thereabout. It is to be noted that the vertical support of the inverted T-shaped holder 421 is offset from the center of the upper cap 522, so that the horizontal lever shaft 422 is also offset from a centerline of the flow-indicating cylinder 52. The shaft holes 411 are provided near one side of the drop carrier 41 corresponding to the offset lever structure 42, so as to center the drop carrier 41 in the cylinder 52. That is, portions of the drop carrier 41 located at two opposite sides of the horizontal lever shaft 422 of the lever structure 42 are not equal in their radial widths. To keep the drop carrier 41 in a balanced horizontal position relative to the inverted T-shaped holder 421 without swaying about the horizontal lever shaft 422, a weighted area 412 is provided on the drop carrier 41 at an outer side of the shaft holes 411.

The drop carrier 41 is also provided at a center with a recess 413 just large enough to accept a momentum of one medicine drop fallen from the medicine dropper 521, and at a position, for example, between the two shaft holes 411 with an upward extended stopping plate 414. The medicine drop fallen from the medicine dropper 521 impacts on the central recess 413 located within the portion of the drop carrier 41 having larger radial width, causing the drop carrier 41 to sway about the horizontal lever shaft 422 as a result of lever action. At this point, the portion of the drop carrier 41 having the larger radial width is tilted-downward to block off a path between the emitter 21 and the receiver 22 of the detecting means 20. The stopping plate 414 is adapted to abut against the vertical support of the inverted T-shaped holder 421 when the drop carrier 41 sways and tilts about the horizontal lever shaft 422, lest the drop carrier 41 should overly sway into a vertical position.

In the illustrated lever structure 42, the horizontal shaft 422 is used as the lever shaft for the drop carrier 41 to pivotally sway thereabout. However, other designs may also be adopted for the lever structure 42. For example, two radially inward projected pivotal shafts may be provided at two diametrically opposite points on an innerwall of the flow-indicating cylinder 52, and the drop carrier 41 may be provided at two diametrically opposite points with corresponding sleeves for engaging with the two pivotal shafts on the cylinder 52.

Please refer to FIG. 4. When the system of the present invention is in use without any medicine drop fallen from the medicine dropper 521 onto the drop carrier 41, the drop carrier 41 is adapted to maintain at a balanced horizontal position in the flow-indicating cylinder 52. At this point, the emitter 21 and the receiver 22 of the detecting means 20 are not isolated from each other, and the electronic control circuits inside the alarm means 30 are set to a disabled state.

Figure 5:
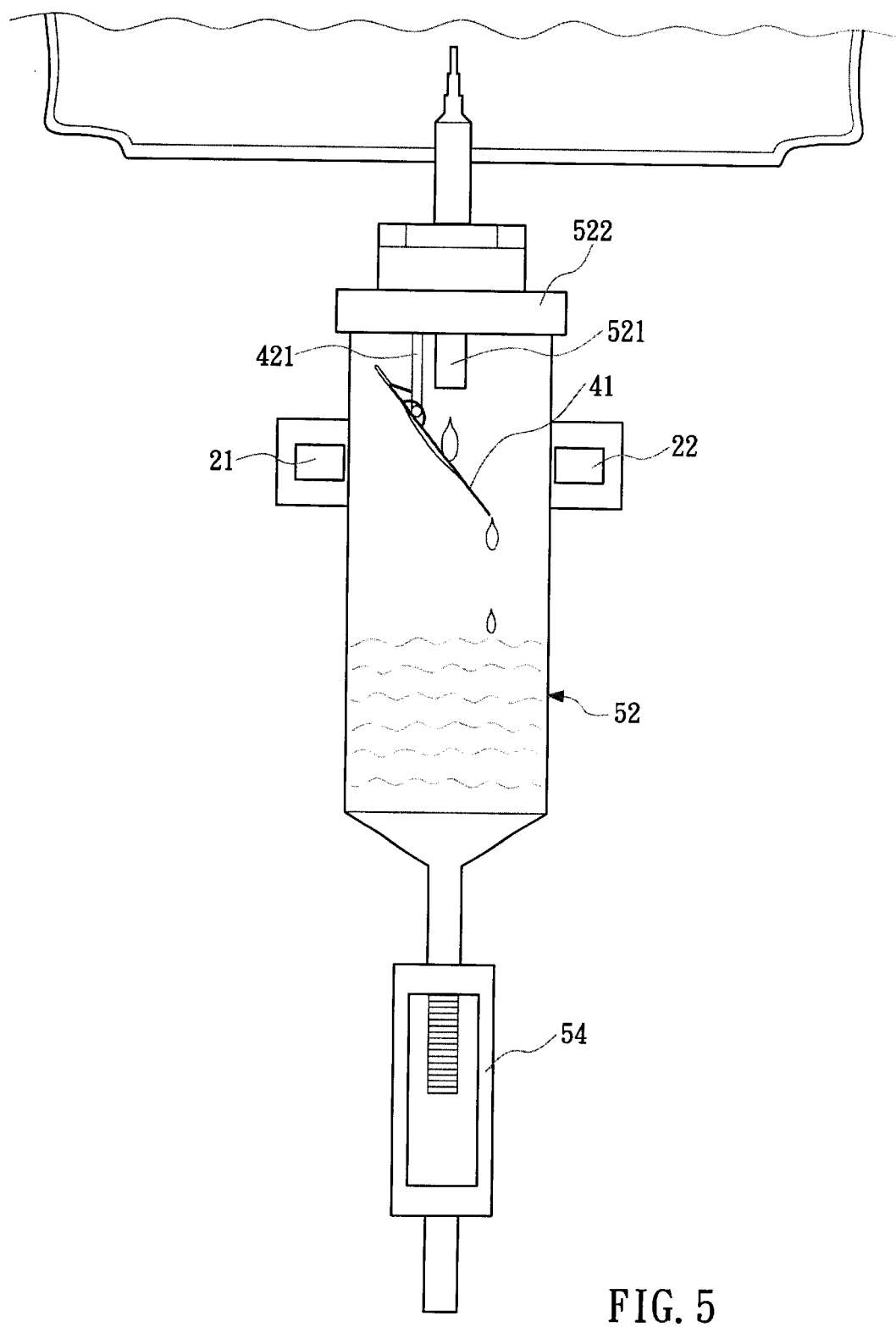
FIG. 5 is another fragmentary side view of the system of the present invention showing the drop carrier in a tilted state caused by a medicine drop fallen thereon.

It is known that the medicine instiller is used to control the speed of a medicine liquid being injected into a patient's vessel, and the injection speed of the medical liquid can be regulated via the flow controller 54. In most cases, the injection speed is set and regulated based on the number of drops per minute, such as six drops per minute, eight drops per minute or the like. When an injection through medicine instillation starts after the number of drops per minute has been set via the flow controller 54, the medicine liquid drips from the medicine dropper 521 drop by drop. That is, the medicine liquid drops from the medicine container 51 into the flow-indicating cylinder 52 intermittently. The intermittent medicine drops impact on the portion of the drop carrier 41 having the longer radial width, and a momentum of each fallen medicine drop would cause the drop carrier 41 to sway about the lever structure 42 and tilt the larger portion downward once, as shown in FIG. 5. The radially wider portion of the tilted drop carrier 41 is now located between the emitter 21 and the receiver 22 of the detecting means 20 to isolate the two elements from each other to cut off the detecting means 20. That is, the swayed drop carrier 41 stops waves of infrared light, for example, emitted from the emitter 21 from being transmitted to the receiver 22.

Since the injection through instillation is set to a stable dripping speed of 6 to 8 drops per minute, an interval between two successive drops is long enough for a first medicine drop fallen on the drop carrier 41 to sway and tilt the same, and then flows off the tilted drop carrier 41 to return the latter to the balanced horizontal position again before a second medicine drop falls. That is, the drop carrier 41 is intermittently and reciprocatingly swayed and tilted, and the emitter 21 and the receiver 22 are intermittently isolated from each other by the tilted drop carrier 41 at a fixed frequency. This type of intermittent isolation at a fixed frequency cycles to form a signal of open or close circuit from the detecting means 20. By designing the electronic control circuits in the alarm mean 30 based on the signals of open and close circuit from the detecting means 20, the number of drops fallen on the drop carrier 41 per minute can be automatically detected and calculated, or converted into an estimate value of flow per minute or speed of medicine drop (because each drop contains almost the same dosage), and a default value serving as a standard of detection may be set and displayed on the display 32 of the alarm means 30.

When the automatic detecting and prewarning system of the present invention is used in an instillation of medicine liquid that has been set to a fixed instilling rate or fixed number of drops per minute, and the detecting means 20 detects an abnormal condition in the actual number of drops or flow of the dripping medicine liquid, which might be caused by a compressed or bent and therefore blocked tube 53, or an improperly adjusted flow controller 54, or an empty medicine container 51, and the instillation does not return normal after a period of time, for example, one minute, set in the electronic control circuits allowed for the abnormal condition has lapsed, the alarm means 30 would then be automatically enabled to emit warnings. Unlike the present invention, conventional warning systems for medicine instiller emit warnings only when the medicine container 51 becomes empty.

Since the system of the present invention allows detection of the fixed number of drops or flow per minute of the medicine liquid being instilled with the medicine instiller and setting of a standard number of drops or flow per minute of the medicine liquid in the alarm means 30, and since each medicine container 51 is generally labeled with a dosage thereof, it is possible to preset for the system of the present invention configured with advanced electronic controlling technologies a time point at which the medicine liquid being instilled might be used up. The preset time value is input to the alarm means 30 or shown on the display 32 before starting using the system of the present invention. In this manner, nursing personnel may watch several medicine instillers at the same time without neglecting the time at which each individual medicine container 51 might become empty. The nursing in patient wards could therefore be efficiently and effectively performed and controlled.

The alarm means 30 is connected to the detecting means 20 via a conductor, a length of which may be properly decided according to actual need. The alarm means 30 may be designed as a buzzer or a loudspeaker to emit musical sound or voice, or as a light-emitting device, such as a bulb, to emit light or flashes of light, or for use with an infrared (IR) or a radio frequency (RF) transmission system to transfer a warning signal to other alarms or nursing stations at remote locations to enable the most effective care of patients. According to the currently available electronic control technologies, designing of such internal circuits and wirings of the detecting means 20 and the alarm means 30 for detecting and setting the number of drops or flow of medicine liquid per minute is an ordinarily accomplishable skill, and is therefore not discussed in more details herein.

What is claimed is:

1. An automatic detecting and prewarning system for medicine instiller, said medicine instiller normally including a medicine liquid container for containing an amount of medicine liquid, a transparent flow-indicating cylinder, a tube, a flow controller, and a syringe, comprising a clamp, detecting means provided on said clamp, alarm means connected to said detecting means, and drop-carrier swaying means;

said clamp being adapted to clamp on an outer surface of said flow-indicating cylinder of said medicine instiller without compressing or deforming said flow-indicating cylinder, and two cavities being correspondingly provided on two opposite jaws of said clamp;

said detecting means including an emitter and a receiver that are separately received in said two cavities on said clamp, such that said emitter and said receiver are spaced by said flow-indicating cylinder to face each other when said clamp is clamped onto said flow-indicating cylinder at a predetermined height;

said alarm means being connected to said detecting means via a conductor to receive signals sent by said detecting means, said alarm means including internal electronic control circuits to provide detecting and setting functions; and said drop-carrier swaying means being disposed inside said flow-indicating cylinder below a medicine dropper centered at and downward extended from an upper cap of said flow-indicating cylinder, and including a lever structure and a drop carrier pivotally and eccentrically connected to a lower end of said lever structure; and said drop carrier being adapted to sway about said lever structure and tilt toward a radially larger side when a medicine drop falls from said medicine dropper to impact on said radially larger side of said drop carrier;

whereby when said clamp is clamped on said flow-indicating cylinder and said medicine instiller is set via said flow controller to instill a medicine liquid at a fixed number of drops per minute, said drop carrier is intermittently impacted by fallen medicine drops to sway and tilt reciprocatingly at a fixed frequency, bringing said radially larger side of said drop carrier to intermittently move into a path between said emitter and said receiver to cut off said detecting means on said clamp, said electronic control circuits inside said alarm means being adapted to detect said intermittently cut off detecting means and set a standard number of drops or flow per minute for said specific medicine instilling operation, and said alarm means being automatically enabled when an abnormal number of drops or flow per minute has continued for a preset time value.

2. The automatic detecting and-prewarning system for medicine instiller as claimed in claim 1, wherein said detecting means is adapted to emit and receive infrared light, magnetic waves or laser.

3. The automatic detecting and prewarning system for medicine instiller as claimed in claim 1, wherein said alarm means is selected from the group consisting of buzzers, loudspeakers, and light emitting devices emitting constant light or flashes of light, and may be used with an infrared (IR) or radio frequency (RF) transmission system to transfer warning signals to other alarms or nursing stations at remote locations.

4. The automatic detecting and prewarning system for medicine instiller as claimed in claim 1, wherein said alarm means is provided with externally accessible switches and display to work with said electronic control circuits inside said alarm means.

* * * * *